(12) United States Patent
Rickard et al.

(10) Patent No.: US 9,615,970 B2
(45) Date of Patent: *Apr. 11, 2017

(54) INTRAOCULAR PRESSURE SENSOR WITH EXTERNAL PRESSURE COMPENSATION

(71) Applicant: ALCON RESEARCH, LTD., Fort Worth, TX (US)

(72) Inventors: Matthew Rickard, Yorba Linda, CA (US); Robert Sanchez, Jr., Oceanside, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 173 days.

This patent is subject to a terminal disclaimer.

(21) Appl. No.: 14/267,443

(22) Filed: May 1, 2014

(65) Prior Publication Data

US 2014/0243731 A1 Aug. 28, 2014

Related U.S. Application Data

(60) Continuation of application No. 13/565,907, filed on Aug. 3, 2012, now abandoned, which is a division of application No. 12/563,244, filed on Sep. 21, 2009, now Pat. No. 8,257,295.

(51) Int. Cl.
*A61F 9/007* (2006.01)
*A61B 3/16* (2006.01)
*A61M 27/00* (2006.01)
*A61B 5/00* (2006.01)

(52) U.S. Cl.
CPC ............ *A61F 9/00781* (2013.01); *A61B 3/16* (2013.01); *A61B 5/6821* (2013.01); *A61M 27/002* (2013.01)

(58) Field of Classification Search
CPC .............................. A61F 9/00781; A61B 3/16
See application file for complete search history.

(56) References Cited

U.S. PATENT DOCUMENTS

| 4,089,329 A | 5/1978 | Couvillion, Jr. et al. |
| 4,206,762 A * | 6/1980 | Cosman ............... A61B 5/0002 600/438 |
| 4,457,757 A | 7/1984 | Molteno |
| 4,604,087 A | 8/1986 | Joseph |

(Continued)

FOREIGN PATENT DOCUMENTS

| CA | 2772359 A1 | 3/2011 |
| DE | 4438201 A1 | 5/1996 |

(Continued)

OTHER PUBLICATIONS

International Searching Authority, International Search Report, PCT/US2012/66709, Apr. 19, 2013, 4 pages.

(Continued)

*Primary Examiner* — Leslie Deak
(74) *Attorney, Agent, or Firm* — Kenneth D. Bassinger

(57) ABSTRACT

An intraocular pressure sensor system has a first pressure sensor located in an anterior chamber of an eye and a remote pressure sensor located remotely from the first pressure sensor. The remote pressure sensor measures or approximates atmospheric pressure. A difference between readings from the first pressure sensor and the remote pressure sensor approximates intraocular pressure.

8 Claims, 3 Drawing Sheets

(56) References Cited

U.S. PATENT DOCUMENTS

| | | |
|---|---|---|
| 4,656,827 A | 4/1987 | Puillet |
| 4,750,901 A | 6/1988 | Molteno |
| 4,869,282 A | 9/1989 | Sittler et al. |
| 4,922,913 A | 5/1990 | Waters, Jr. et al. |
| 5,005,577 A | 4/1991 | Frenkel |
| 5,083,742 A | 1/1992 | Wylie et al. |
| 5,178,604 A | 1/1993 | Baerveldt et al. |
| 5,179,953 A | 1/1993 | Kursar |
| 5,397,300 A | 3/1995 | Baerveldt et al. |
| 5,466,233 A | 11/1995 | Weiner et al. |
| 5,476,445 A | 12/1995 | Baerveldt et al. |
| 5,558,629 A | 9/1996 | Baerveldt et al. |
| 5,573,646 A | 11/1996 | Saito et al. |
| 5,626,558 A | 5/1997 | Suson |
| 5,681,275 A | 10/1997 | Ahmed |
| 5,702,618 A | 12/1997 | Saaski et al. |
| 5,707,643 A | 1/1998 | Ogura et al. |
| 5,722,948 A | 3/1998 | Gross |
| 5,891,097 A | 4/1999 | Saito et al. |
| 5,910,110 A | 6/1999 | Bastable |
| 6,007,511 A | 12/1999 | Prywes |
| 6,048,328 A | 4/2000 | Haller et al. |
| 6,050,970 A | 4/2000 | Baerveldt |
| 6,251,090 B1 | 6/2001 | Avery et al. |
| 6,261,256 B1 | 7/2001 | Ahmed |
| 6,443,893 B1 | 9/2002 | Schnakenberg et al. |
| 6,447,449 B1 | 9/2002 | Fleischman et al. |
| 6,468,283 B1 | 10/2002 | Richter et al. |
| 6,533,733 B1 | 3/2003 | Ericson et al. |
| 6,579,235 B1 | 6/2003 | Abita et al. |
| 6,589,198 B1 | 7/2003 | Soltanpour et al. |
| 6,682,500 B2 | 1/2004 | Soltanpour et al. |
| 6,712,764 B2 | 3/2004 | Jeffries et al. |
| 6,719,750 B2 | 4/2004 | Varner et al. |
| 6,726,676 B2 | 4/2004 | Stegmann et al. |
| 6,749,568 B2 | 6/2004 | Fleischman et al. |
| 6,939,299 B1 | 9/2005 | Petersen et al. |
| 6,962,573 B1 | 11/2005 | Wilcox |
| 6,976,982 B2 | 12/2005 | Santini, Jr. et al. |
| 7,025,740 B2 | 4/2006 | Ahmed |
| 7,137,952 B2 | 11/2006 | Leonardi et al. |
| 7,169,106 B2 | 1/2007 | Fleischman et al. |
| 7,252,006 B2 | 8/2007 | Tai et al. |
| 7,304,334 B2 | 12/2007 | Agarwal et al. |
| 7,354,416 B2 | 4/2008 | Quiroz-Mercado et al. |
| 7,409,863 B2 | 8/2008 | Bateman et al. |
| 7,612,328 B2 | 11/2009 | Kaiser |
| 7,648,465 B2 | 1/2010 | Gordon |
| 7,756,559 B2 | 7/2010 | Abreu |
| 7,824,699 B2 | 11/2010 | Ralph et al. |
| 8,123,687 B2 | 2/2012 | Dacquay et al. |
| 8,182,435 B2 | 5/2012 | Dacquay et al. |
| 8,206,440 B2 | 6/2012 | Guarnieri |
| 8,257,295 B2 | 9/2012 | Rickard et al. |
| 8,419,673 B2 | 4/2013 | Rickard |
| 8,545,431 B2 | 10/2013 | Rickard |
| 8,549,925 B2 | 10/2013 | Tai et al. |
| 8,579,848 B2 | 11/2013 | Field et al. |
| 8,585,631 B2 | 11/2013 | Dacquay |
| 8,814,820 B2 | 8/2014 | Bergheim et al. |
| 8,840,578 B2 | 9/2014 | Dos Santos et al. |
| 2001/0000527 A1 | 4/2001 | Yaron et al. |
| 2002/0013546 A1 | 1/2002 | Grieshaber et al. |
| 2002/0019607 A1 | 2/2002 | Bui |
| 2002/0049374 A1 | 4/2002 | Abreu |
| 2002/0087111 A1 | 7/2002 | Ethier et al. |
| 2002/0099359 A1 | 7/2002 | Santini, Jr. et al. |
| 2002/0103412 A1 | 8/2002 | Trimmer |
| 2002/0139947 A1 | 10/2002 | Wang |
| 2002/0143284 A1 | 10/2002 | Tu et al. |
| 2002/0156461 A1 | 10/2002 | Joshi |
| 2002/0175191 A1 | 11/2002 | Joshi et al. |
| 2002/0193674 A1 | 12/2002 | Fleischman et al. |
| 2003/0014036 A1 | 1/2003 | Varner et al. |
| 2003/0078487 A1 | 4/2003 | Jeffries et al. |
| 2003/0225318 A1 | 12/2003 | Montegrande et al. |
| 2004/0013702 A1 | 1/2004 | Glover |
| 2004/0059248 A1 | 3/2004 | Messner et al. |
| 2004/0073137 A1 | 4/2004 | Lloyd et al. |
| 2004/0111050 A1 | 6/2004 | Smedley et al. |
| 2004/0116794 A1 | 6/2004 | Fink et al. |
| 2004/0186367 A1 | 9/2004 | Fresco |
| 2004/0254438 A1 | 12/2004 | Chuck et al. |
| 2004/0254517 A1 | 12/2004 | Quiroz-Mercado et al. |
| 2005/0016866 A1 | 1/2005 | Kramer et al. |
| 2005/0049578 A1 | 3/2005 | Tu et al. |
| 2005/0159660 A1 | 7/2005 | Montegrande et al. |
| 2005/0271704 A1 | 12/2005 | Tu et al. |
| 2005/0273033 A1 | 12/2005 | Grahn et al. |
| 2006/0041220 A1 | 2/2006 | Boukhny et al. |
| 2006/0131350 A1 | 6/2006 | Schechter et al. |
| 2006/0189916 A1 | 8/2006 | Bas |
| 2007/0019156 A1 | 1/2007 | Fink |
| 2007/0032757 A1 | 2/2007 | Medow et al. |
| 2007/0077270 A1 | 4/2007 | Wen |
| 2007/0106199 A1 | 5/2007 | Krivoy et al. |
| 2007/0106200 A1 | 5/2007 | Levy |
| 2007/0109117 A1 | 5/2007 | Heitzmann et al. |
| 2007/0123767 A1 | 5/2007 | Montegrande et al. |
| 2007/0129623 A1 | 6/2007 | Fleischmann et al. |
| 2007/0156079 A1 | 7/2007 | Brown |
| 2007/0212397 A1 | 9/2007 | Roth |
| 2007/0255262 A1 | 11/2007 | Haase |
| 2008/0015421 A1 | 1/2008 | Penner |
| 2008/0027478 A1 | 1/2008 | Connors et al. |
| 2008/0077127 A1 | 3/2008 | Gao et al. |
| 2008/0097276 A1 | 4/2008 | Bertrand et al. |
| 2008/0125691 A1 | 5/2008 | Yaron et al. |
| 2008/0129486 A1 | 6/2008 | Jeckelmann et al. |
| 2008/0147021 A1 | 6/2008 | Jani |
| 2008/0228127 A1 | 9/2008 | Burns et al. |
| 2008/0257915 A1 | 10/2008 | Wold |
| 2009/0069648 A1 | 3/2009 | Irazqui et al. |
| 2009/0076367 A1 | 3/2009 | Sit et al. |
| 2009/0143713 A1 | 6/2009 | Van Dam et al. |
| 2009/0227933 A1 | 9/2009 | Karageozian |
| 2009/0240215 A1 | 9/2009 | Humayun et al. |
| 2009/0275924 A1 | 11/2009 | Lattanzio et al. |
| 2009/0312742 A1 | 12/2009 | Pang et al. |
| 2010/0010416 A1 | 1/2010 | Juan, Jr. et al. |
| 2010/0042209 A1 | 2/2010 | Guarnieri |
| 2010/0114006 A1 | 5/2010 | Baerveldt |
| 2010/0121248 A1 | 5/2010 | Yu et al. |
| 2010/0121348 A1 | 5/2010 | van der Burg et al. |
| 2010/0174272 A1 | 7/2010 | Weiner |
| 2010/0222769 A1 | 9/2010 | Meng et al. |
| 2010/0222770 A1 | 9/2010 | Gordon et al. |
| 2010/0234717 A1 | 9/2010 | Wismer |
| 2010/0253167 A1 | 10/2010 | Charnley et al. |
| 2010/0280349 A1 | 11/2010 | Dacquay et al. |
| 2010/0305550 A1 | 12/2010 | Meng et al. |
| 2011/0046536 A1 | 2/2011 | Stegmann et al. |
| 2011/0071454 A1 | 3/2011 | Dos Santos et al. |
| 2011/0071456 A1 | 3/2011 | Rickard |
| 2011/0071458 A1 | 3/2011 | Rickard |
| 2011/0071459 A1 | 3/2011 | Rickard et al. |
| 2011/0071505 A1 | 3/2011 | Rickard et al. |
| 2011/0077626 A1 | 3/2011 | Baerveldt et al. |
| 2011/0248671 A1 | 10/2011 | Dos Santos et al. |
| 2012/0004528 A1 | 1/2012 | Li et al. |
| 2012/0022505 A1 | 1/2012 | Dacquay et al. |
| 2012/0022506 A1 | 1/2012 | Rickard et al. |
| 2012/0296258 A1 | 11/2012 | Rickard et al. |
| 2013/0085440 A1 | 4/2013 | Bohm et al. |
| 2013/0144202 A1 | 6/2013 | Field et al. |
| 2013/0150775 A1 | 6/2013 | Dos Santos et al. |
| 2013/0150777 A1 | 6/2013 | Bohm et al. |
| 2013/0204177 A1 | 8/2013 | Field et al. |
| 2013/0218064 A1 | 8/2013 | Rickard |

(56) References Cited

U.S. PATENT DOCUMENTS

| | | |
|---|---|---|
| 2013/0338564 A1 | 12/2013 | Rickard et al. |
| 2014/0039374 A1 | 2/2014 | Dos Santos et al. |

FOREIGN PATENT DOCUMENTS

| | | |
|---|---|---|
| EP | 0102747 A1 | 3/1984 |
| EP | 1195523 A2 | 4/2002 |
| EP | 1917987 A2 | 5/2008 |
| EP | 2427097 A1 | 3/2012 |
| JP | 03049775 | 3/1991 |
| WO | 9303665 A1 | 3/1993 |
| WO | 9803665 A1 | 1/1998 |
| WO | 9803809 A1 | 1/1998 |
| WO | 9938470 A2 | 8/1999 |
| WO | 0174427 A1 | 10/2001 |
| WO | 0194784 A1 | 12/2001 |
| WO | 02056758 A1 | 7/2002 |
| WO | 03001991 A1 | 1/2003 |
| WO | 03102632 A2 | 12/2003 |
| WO | 2004014218 A2 | 2/2004 |
| WO | 2005079204 A2 | 9/2005 |
| WO | 2005088417 A1 | 9/2005 |
| WO | 2007127305 A2 | 11/2007 |
| WO | 2007136993 A1 | 11/2007 |
| WO | 2008060649 A2 | 5/2008 |
| WO | 2008061043 A2 | 5/2008 |
| WO | 2008084350 A2 | 7/2008 |
| WO | 2008094672 A2 | 8/2008 |
| WO | 2008084350 A3 | 10/2008 |
| WO | 2008094672 A3 | 11/2008 |
| WO | 2009010799 A2 | 1/2009 |
| WO | 2009026499 A1 | 2/2009 |
| WO | 2009049686 A1 | 4/2009 |
| WO | 2009081031 A2 | 7/2009 |
| WO | 2010129446 A1 | 11/2010 |
| WO | 2011034727 A1 | 3/2011 |
| WO | 2011034738 A1 | 3/2011 |
| WO | 2011034740 A1 | 3/2011 |
| WO | 2011034742 A2 | 3/2011 |
| WO | 2011035218 A1 | 3/2011 |
| WO | 2012012017 A1 | 1/2012 |
| WO | 2013085894 A2 | 6/2013 |
| WO | 2013085895 A1 | 6/2013 |
| WO | 2013090006 | 6/2013 |
| WO | 2013090231 A1 | 6/2013 |
| WO | 2013123142 A1 | 8/2013 |

OTHER PUBLICATIONS

International Searching Authority, Written Opinion of the International Searching Authority, PCT/US2012/66709, Apr. 19, 2013, 5 pages.

Parkhutik, Vitali, et al., The Role of Hydrogen in the Formation of Porous Structures in Silicon, Materials Science & Engineering, 1999, B58, 95-99, Elsevier Science, S.A.

Van Schuylenbergh, K., et al, "An Implantable Telemetric Tonometer for Direct Intraocular Pressure Measurements," 1st European Conference on Biomedical Engineering, Feb. 1991, pp. 194-195, vol. 17, No. 20, Nice, France.

Walter, Peter; Intraocular Pressure Sensor: Where Are We—Where Will We Go? Journal Graefe's Archive for Clinical and Experimental Ophthalmology; Publisher Springer Berline/Heidelberg; ISSN 0721-832X (Print) 1435-702X (Online); Issue vol. 240, No. 5/May 2002 DOI 10.1007/s00417-002-0474-y; pp. 335-336; Subject Collection Medicine.

Neagu Cristina R.; "A Medical Microactuator Based on an Electrochemical Principle"; Thesis at the Twente University,the Netherlands, Enschede; Aug. 28, 1998; pp. 1-162.

Saloomeh Saati M.D., et al.; "Mini Drug Pump for Ophthalmic Use"; Trans Am Ophthalmol Soc 2009; 107; pp. 60-71.

Stemme et al.; "A Valveless Diffuser/Nozzle-Based Fluid Pump"; ScienceDirect; Sensors and Actuators A, 39; pp. 159-167 (1993).

Nisar, et al.; MEMS-Based Micropumps in Drug Delivery and Biomedical Applications; ScienceDirect; Sensors and Actuators B 130; pp. 917-942 (2008).

International Searching Authority, Search Report and Written Opinion of the International Searching Authority PCT US2010/047605; Dec. 16, 2010.

International Searching Authority, Search Report and Written Opinion of the International Searching Authority PCT/US2010/047612; Dec. 21, 2010.

Driot et al.; "Ocular pharmacokinetics of fluocinolone acetonide after RetisertTM intravitreal implantation in rabbits over a 1-year period"; J. Ocular Pharm; 20; 3;pp. 269-275.

Glybina et al.; "Neuroprotective properties of fluocinolone acetonide chronically delivered into the vitreous of albino RCS rats"; IVOS; 47; ARVO e-Abstract 1028.

Kuppermann B D et al., 2006, "Efficacy and safety of a novel intravitreous dexamethasone drug-delivery system after applicator or incisional placement in patients with macular edema", IOVS, 47 ARVO E-Abs 5913.

Miyamoto H et al., 1997, Biodegradable scleral implant for intravitreal controlled release of fluconazole, Curr Eye Res, 16(9), 930-935.

Mruthyunjaya P et al., 2003, "An intravitreal sustained release fluocinolone acetonide device to treat severe experimental uveitis", IOVS, 44, ARVO E-Abs 4215.

Ratanapakorn T et al., 2005, "Helical intravitreal triamcinolone implant: An explanation survival study", IVOS 46 E-Abs 484.

Rego MGR et al., 2004, "In vitro evaluation of sustained-release intravitreal dexamethasone implants", IOVS, 45 E-Abs 5060.

Sakurai E et al., 2001, "Scleral plug of biodegradable polymers containing ganciclovir for experimental cytomegalovirus retinitis", IOVS, 42(9), 2043-2048.

See R F et al., 2006, "Safety and drug release profile of injectable intravitreal sustained-release fluocinolone acetonide device", IOVS, 47, ARVO E-Abs 5119.

Tano R et al., 2005, Helical intravitreal implant: surgical method development and outcomes, IOVS, 46, ARVO E-Abs 483.

Varner S E et al., 2003, "Development of a minimally invasive intravitreal implant for drug delivery", IOVS, 44, ARVO E-Abs 4214.

Weiner A L, 2007, "Drug Delivery Systems in Ophthalmic Applications, In: Ocular Therapeutics; Eye on New Discoveries; T. Yorio, A. Clark, M.Wax, Eds, Elsevier Press/Academic Press, New York", pp. 7-43.

Yasukawa T et al., 2001, "Biodegradable scleral plugs for vitreoretinal drug delivery", Adv. Drug Del Rev., 52(1), 25-36.

International Searching Authority, International Search Report and Written Opinion of the International Searching Authority PCT/US2013/026066, Apr. 17, 2013, 5 pages.

International Searching Authority, Search Report and Written Opinion of the International Searching Authority PCT/US2012/068878 dated Apr. 3, 2013.

International Searching Authority, Search Report and Written Opinion of the International Searching Authority dated Apr. 2, 2013; PCT/US2012/067747.

International Searching Authority, Partial Search Report PCT/US2012/067741; dated Apr. 2, 2013, 6 pages.

Byunghoon Bae, Hongseok Kee, Seonho Kim, Yeon Lee, Taeseok Sim, Yongkweon Him and Kyihwan Park; "In Vitro Experiment of the Pressure Regulating Valve for a Glaucoma Impact"; Journal of Micromechanics and Microengineering, 13 (2003); pp. 613-619.

Eggers, T., et al, "Wireless Intra-Ocular Pressure Monitoring System Integrated Into an Artificial Lens," 1st Annual Int'l IEEE-EMBS Special Topic Conference on Microtechnologies in Medicine & Biology, Oct. 12-14, 2000, pp. 466-469, Lyon, France.

Greene, M.E. and Gilman, B.G., "Intraocular Pressure Measurement With Instrumented Contact Lenses," Investigative Ophthalmology & Visual Science (IVOS), Apr. 1974, pp. 299-302, vol. 13, No. 4, IVOS.

Hjortdal, Jesper and Jensen, Peter, "In Vitro Measurement of Corneal Strain, Thickness, and Curvature Using Digital Image Processing," Acta Ophthalmologica Scandinavica, 1995, pp. 5-11, vol. 73, Denmark.

(56) References Cited

OTHER PUBLICATIONS

International Searching Authority, Search Report and Written Opinion of the International Searching Authority, PCT/US2010/033329, Jul. 13, 2010, 14 pages.
International Searching Authority, Search Report and Written Opinion of the International Searching Authority, PCT/US2010/047429, Nov. 1, 2010, 15 pages.
International Searching Authority, Search Report and Written Opinion of the International Searching Authority, PCT/US2010/047600, Dec. 14, 2010, 13 pages.
International Searching Authority, Search Report and Written Opinion of the International Searching Authority, PCT/US2010/049424, Nov. 26, 2010, 15 pages.
International Searching Authority, Search Report and Written Opinion of the International Searching Authority, PCT/US2011/036742, Aug. 17, 2011, 2 pages.
Lam, Andrew K.C. and Douthwaite, William A., "The Effect of an Artificially Intraocular Pressure on the Central Corneal Curvature," Ophthalmic and Physiological Optics, 1997, pp. 18-24, vol. 17, No. 1, Elsevier Science, Ltd., Great Britain.
Leonardi, Matteo, et al., "A Soft Contact Lens With a Mems Strain Gage Embedded for Intraocular Pressure Monitoring," In Proc. 12th Int'l Conference on Solid State Sensors, Actuators and Microsystems, Jun. 8-12, 2003, pp. 1043-1046, vol. 2, Boston, MA.
Leonardi, Matteo, et al., "First Steps Toward Noninvasive Intraocular Pressure Monitoring with a Sensing Contact Lens," Investigative Ophthalmology & Visual Science (IVOS), 2004, pp. 3113-3117, vol. 45, No. 9, IVOS.
McLaren, Jay W., et al, "Continuous Measurement of Intraocular Pressure in Rabbits by Telemetry," Investigative Ophthalmology & Visual Science (IVOS), May 1996, pp. 966-975, vol. 37, No. 6, IVOS.
Mokwa, Wilfried, et al, "Micro-Transponder Systems for Medical Applications," IEEE Transactions on Instrumentation and Measurement, Dec. 2001, pp. 1551-1555, vol. 50, No. 6, IEEE, Germany.
Puers, Robert, "Linking Sensors with Telemetry: Impact on the System Design," In Proc. 8th Int'l Conference of Solid State Sensors, Actuators, Eurosens, Jun. 25-29, 1995, pp. 169-174, Stockholm, Sweden.
Schnakenberg, U., et al, "Initial Investigations on Systems for Measuring Intraocular Pressure," Sensors and Actuators, 2000, p. 287-291, vol. 85, Elsevier Science B.V., Germany.
Stangel, Karsten, et al, "A Programmable Intraocular CMOS Pressure Sensor System Implant," IEEE Journal of Solid-State Circuits, Jul. 2001, pp. 1094-1100, vol. 36, No. 7, IEEE, Germany.
Ullerich, Stella, et al, "Micro Coils for an Advanced System for Measuring Intraocular Pressure," 1st Annual Int'l IEEE-EMBS Special Topic Conference on Microtechnologies in Medicine & Biology, Oct. 12-14, 2000, pp. 470-474, Lyon, France.

\* cited by examiner

INTRAOCULAR PRESSURE SENSOR WITH EXTERNAL PRESSURE COMPENSATION

RELATED APPLICATIONS

This application is a continuation of U.S. application Ser. No. 13/565,907, filed Aug. 3, 2012 which is a division of U.S. application Ser. No. 12/563,244 filed Sep. 21, 2009, now U.S. Pat. No. 8,257,295.

BACKGROUND OF THE INVENTION

The present invention relates to a device for monitoring intraocular pressure and more particularly to an implantable pressure sensor with external pressure compensation.

Glaucoma, a group of eye diseases affecting the retina and optic nerve, is one of the leading causes of blindness worldwide. Glaucoma results when the intraocular pressure (IOP) increases to pressures above normal for prolonged periods of time. IOP can increase due to an imbalance of the production of aqueous humor and the drainage of the aqueous humor. Left untreated, an elevated IOP causes irreversible damage the optic nerve and retinal fibers resulting in a progressive, permanent loss of vision.

The eye's ciliary body epithelium constantly produces aqueous humor, the clear fluid that fills the anterior chamber of the eye (the space between the cornea and iris). The aqueous humor flows out of the anterior chamber through the uveoscleral pathways, a complex drainage system. The delicate balance between the production and drainage of aqueous humor determines the eye's IOP.

Open angle (also called chronic open angle or primary open angle) is the most common type of glaucoma. With this type, even though the anterior structures of the eye appear normal, aqueous fluid builds within the anterior chamber, causing the IOP to become elevated. Left untreated, this may result in permanent damage of the optic nerve and retina. Eye drops are generally prescribed to lower the eye pressure. In some cases, surgery is performed if the IOP cannot be adequately controlled with medical therapy.

Only about 10% of the population suffers from acute angle closure glaucoma. Acute angle closure occurs because of an abnormality of the structures in the front of the eye. In most of these cases, the space between the iris and cornea is more narrow than normal, leaving a smaller channel for the aqueous to pass through. If the flow of aqueous becomes completely blocked, the IOP rises sharply, causing a sudden angle closure attack.

Secondary glaucoma occurs as a result of another disease or problem within the eye such as: inflammation, trauma, previous surgery, diabetes, tumor, and certain medications. For this type, both the glaucoma and the underlying problem must be treated.

FIG. 1 is a diagram of the front portion of an eye that helps to explain the processes of glaucoma. In FIG. 1, representations of the lens 110, cornea 120, iris 130, ciliary bodies 140, trabecular meshwork 150, and Schlemm's canal 160 are pictured. Anatomically, the anterior chamber of the eye includes the structures that cause glaucoma. Aqueous fluid is produced by the ciliary bodies 140 that lie beneath the iris 130 and adjacent to the lens 110 in the anterior chamber. This aqueous humor washes over the lens 110 and iris 130 and flows to the drainage system located in the angle of the anterior chamber. The angle of the anterior chamber, which extends circumferentially around the eye, contains structures that allow the aqueous humor to drain. The first structure, and the one most commonly implicated in glaucoma, is the trabecular meshwork 150. The trabecular meshwork 150 extends circumferentially around the anterior chamber in the angle. The trabecular meshwork 150 seems to act as a filter, limiting the outflow of aqueous humor and providing a back pressure producing the IOP. Schlemm's canal 160 is located beyond the trabecular meshwork 150. Schlemm's canal 160 has collector channels that allow aqueous humor to flow out of the anterior chamber. The two arrows in the anterior chamber of FIG. 1 show the flow of aqueous humor from the ciliary bodies 140, over the lens 110, over the iris 130, through the trabecular meshwork 150, and into Schlemm's canal 160 and its collector channels.

In glaucoma patients, IOP can vary widely during a 24 hour period. Generally, IOP is highest in the early morning hours before medication is administered upon waking. Higher pressures damage the optic nerve and can lead to blindness. Accordingly, it would be desirable to measure IOP over time in order to assess the efficacy of various treatments. In addition, continuous IOP data can be used as part of a feedback mechanism to support an implanted active IOP-controlling system (e.g. valve or pump for controlling aqueous humor flow or delivering drugs). The present invention provides an IOP measuring device.

SUMMARY OF THE INVENTION

In one embodiment consistent with the principles of the present invention, the present invention is an intraocular pressure sensor system that has a first pressure sensor located in or in fluidic communication with the anterior chamber of an eye and a remote pressure sensor located remotely from the first pressure sensor. The remote pressure sensor measures or approximates atmospheric pressure. A difference between readings from the first pressure sensor and the remote pressure sensor approximates intraocular pressure.

In another embodiment consistent with the principles of the present invention, the present invention is an intraocular pressure sensor system has a first pressure sensor located in an anterior chamber of an eye and a second pressure sensor located in a drainage location. A difference between readings from the first pressure sensor and the second pressure sensor approximates a pressure differential between the anterior chamber and the drainage location.

In another embodiment consistent with the principles of the present invention, the present invention is an intraocular pressure sensor system has a first pressure sensor located in a drainage location and a remote pressure sensor located remotely from the first pressure sensor. The remote pressure sensor measures or approximates atmospheric pressure. A difference between readings from the first pressure sensor and the remote pressure sensor approximates pressure in the drainage location.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 1:
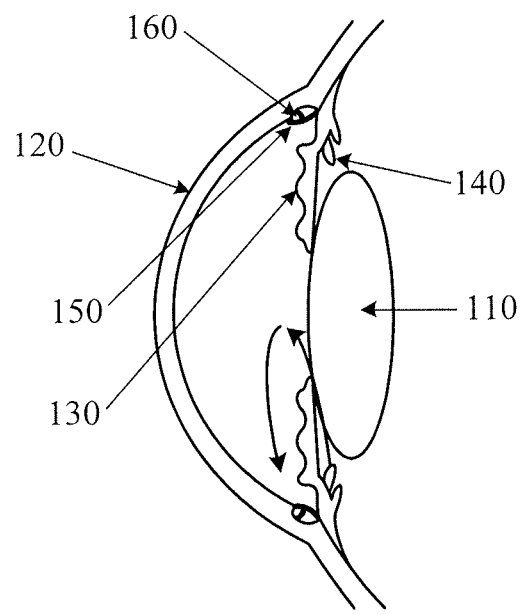
FIG. 1 is a diagram of the front portion of an eye.
Figure 2:
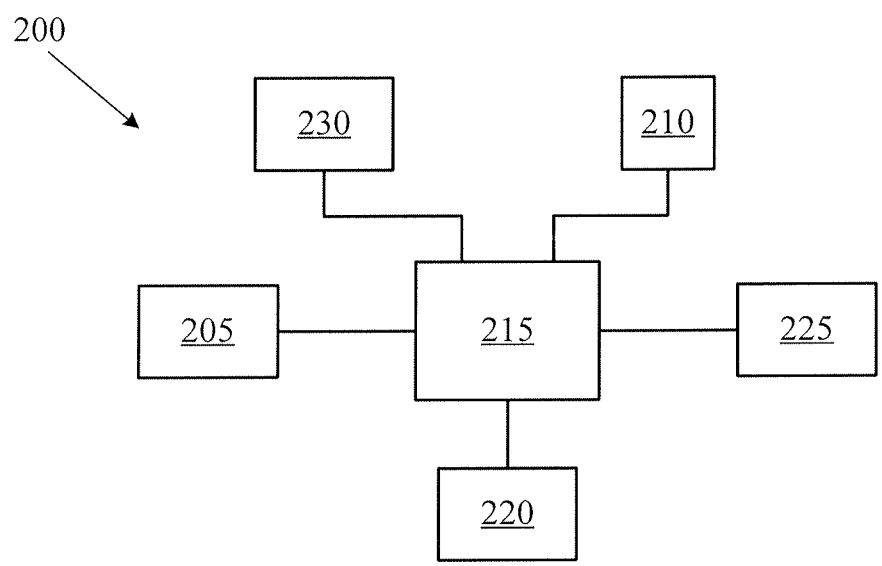
FIG. 2 is a block diagram of an IOP measuring system according to the principles of the present invention.

FIG. 2 is a block diagram of an IOP measuring system 200 according to the principles of the present invention. In FIG. 2, the IOP measuring system includes power source 205, IOP sensor 210 (which can include P1, P2, and/or P3), processor 215, memory 220, data transmission module 225, and optional speaker 230.

Power source 205 is typically a rechargeable battery, such as a lithium ion or lithium polymer battery, although other types of batteries may be employed. In addition, any other type of power cell is appropriate for power source 205. Power source 205 provides power to the system 200, and more particularly to processor 215. Power source can be recharged via an RFID link or other type of magnetic coupling.

Processor 215 is typically an integrated circuit with power, input, and output pins capable of performing logic functions. In various embodiments, processor 215 is a targeted device controller. In such a case, processor 215 performs specific control functions targeted to a specific device or component, such as a data transmission module 225, speaker 230, power source 205, or memory 220. In other embodiments, processor 215 is a microprocessor. In such a case, processor 215 is programmable so that it can function to control more than one component of the device. In other cases, processor 215 is not a programmable microprocessor, but instead is a special purpose controller configured to control different components that perform different functions.

Memory 220 is typically a semiconductor memory such as NAND flash memory. As the size of semiconductor memory is very small, and the memory needs of the system 200 are small, memory 220 occupies a very small footprint of system 200. Memory 220 interfaces with processor 215. As such, processor 215 can write to and read from memory 220. For example, processor 215 can be configured to read data from the IOP sensor 210 and write that data to memory 220. In this manner, a series of IOP readings can be stored in memory 220. Processor 215 is also capable of performing other basic memory functions, such as erasing or overwriting memory 220, detecting when memory 220 is full, and other common functions associated with managing semiconductor memory.

Data transmission module 225 may employ any of a number of different types of data transmission. For example, data transmission module 225 may be active device such as a radio. Data transmission module 225 may also be a passive device such as the antenna on an RFID tag. In this case, an RFID tag includes memory 220 and data transmission module 225 in the form of an antenna. An RFID reader can then be placed near the system 200 to write data to or read data from memory 220. Since the amount of data typically stored in memory 220 is likely to be small (consisting of IOP readings over a period of time), the speed with which data is transferred is not crucial. Other types of data that can be stored in memory 220 and transmitted by data transmission module 225 include, but are not limited to, power source data (e.g. low battery, battery defect), speaker data (warning tones, voices), IOP sensor data (IOP readings, problem conditions), and the like.

Optional speaker 230 provides a warning tone or voice to the patient when a dangerous condition exists. For example, if IOP is at a level that is likely to lead to damage or presents a risk to the patient, speaker 230 may sound a warning tone to alert the patient to seek medical attention or to administer eye drops. Processor 215 reads IOP measurements from IOP sensor 210. If processor 215 reads one or a series of IOP measurements that are above a threshold, then processor 215 can operate speaker 230 to sound a warning. The threshold can be set and stored in memory 220. In this manner, an IOP threshold can be set by a doctor, and when exceeded, a warning can be sounded.

Alternatively, data transmission module may be activated to communicate an elevated IOP condition to a secondary device such as a PDA, cell phone, computer, wrist watch, custom device exclusively for this purpose, remote accessible data storage site (e.g. an internet server, email server, text message server), or other electronic device. In one embodiment, a personal electronic device uploads the data to the remote accessible data storage site (e.g. an internet server, email server, text message server). Information may be uploaded to a remote accessible data storage site so that it can be viewed in real time, for example, by medical personnel. In this case, the secondary device may contain the speaker 230. For example, in a hospital setting, after a patient has undergone glaucoma surgery and had system 200 implanted, a secondary device may be located next to the patient's hospital bed. Since IOP fluctuations are common after glaucoma surgery (both on the high side and on the low side which is also a dangerous condition), processor 215 can read IOP measurements made by an implanted IOP sensor 210. If processor 215 reads an unsafe IOP condition, data transmission module 225 can alert the patient and medical staff via speaker 230 or by transmitting the unsafe readings to a secondary device.

Such a system is also suitable for use outside a hospital setting. For example, if an unsafe IOP condition exists, processor 215 can operate speaker 230 to sound an audible warning. The patient is then alerted and can seek medical attention. The warning can be turned off by a medical professional in a number of ways. For example, when data transmission module 225 is an RFID tag, an RFID link can be established between an external device and system 200. This external device can communicate with system 200 to turn off the speaker 230. Alternatively, an optical signal may be read by system 200. In this case, data transmission module 225 has an optical receptor that can receive a series of light pulses that represent a command—such as a command to turn off speaker 230.

Figure 3:
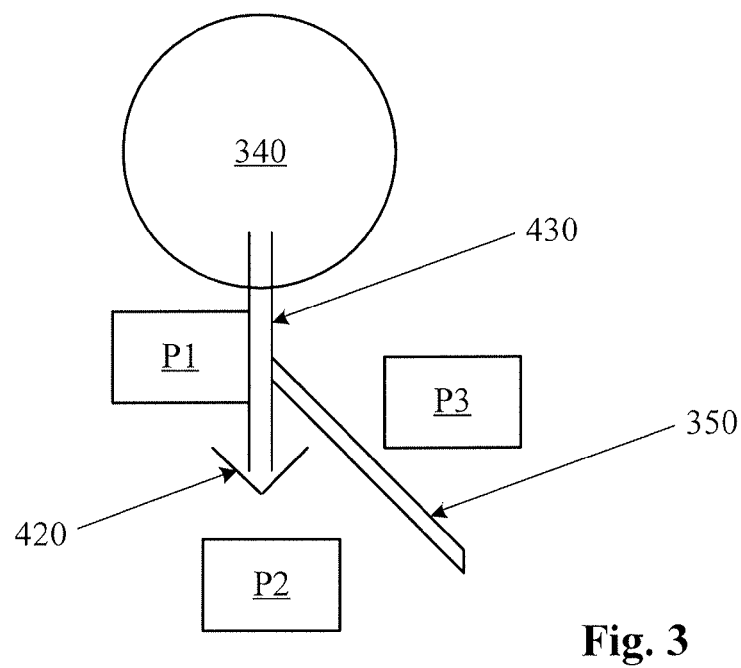
FIG. 3 is a diagram of an IOP sensor according to the principles of the present invention.

FIG. 3 is a diagram of an IOP sensor according to the principles of the present invention. In FIG. 3, the IOP sensor consists of three pressure sensors, P1, P2, and P3, a drainage tube 430, valve 420, and divider 350. Pressure sensor P1 is located in or is in fluidic communication with the anterior chamber 340, pressure sensor P2 is located at a drainage site in the subconjunctival space, and pressure sensor P3 is located remotely from P1 and P2. Pressure sensor P1 can also be located in a lumen or tube that is in fluid communication with the anterior chamber. As such, pressure sensor P1 measures a pressure in the anterior chamber, pressure sensor P2 measures a pressure at a drainage site, and pressure sensor P3 generally measures or corresponds to atmospheric pressure.

In FIG. 3, tube 430 drains aqueous from the anterior chamber 340 of the eye. A valve 420 controls the flow of aqueous through the tube 430. Pressure sensor P1 measures the pressure in the tube 430 upstream from the valve 420 and downstream from the anterior chamber 340. In this manner, pressure sensor P1 measures the pressure in the anterior chamber 340. The expected measurement discrepancy between the true anterior chamber pressure and that measured by P1 when located in a tube downstream of the anterior chamber (even when located between the sclera and the conjunctiva) is very minimal. For example, Poiseuille's law for pipe flow predicts a pressure drop of 0.01 mmHg across a 5-millimeter long tube with a 0.300 millimeter inner diameter for a flow rate of 3 microliters per minute of water.

A divider 350 separates pressure sensor P2 from pressure sensor P3. Pressure sensor P2 is located at a drainage site (e.g. 410 in FIG. 4). As such, pressure sensor P2 is located in a pocket that generally contains aqueous—it is in a wet location. Pressure sensor P3 is physically separated from pressure sensor P2 by divider 350. Divider 350 is a physical structure that separates the wet location of P2 from the dry location of P3. Divider 350 is included when the system of the present invention is located on a single substrate. In this configuration, all three pressure sensors (P1, P2, and P3) are located on a substrate that includes tube 430, valve 420, divider 350, and the other components of the system.

In one embodiment of the present invention, pressure sensor P3 is located in close proximity to the eye. Pressure sensor P3 may be implanted in the eye under the conjunctiva. In such a case, pressure sensor P3 measures a pressure that can be correlated with atmospheric pressure. For example, true atmospheric pressure can be a function of the pressure reading of pressure sensor P3. P3 may also be located in a dry portion of the subconjunctival space, separate from the drainage location. Regardless of location, pressure sensor P3 is intended to measure atmospheric pressure in the vicinity of the eye or at the eye's surface.

Generally, IOP is a gauge pressure reading—the difference between the absolute pressure in the eye (as measured by P1) and atmospheric pressure (as measured by P3). Atmospheric pressure, typically about 760 mm Hg, often varies in magnitude by 10 mmHg or more. For example, atmospheric pressure can vary significantly if a patient goes swimming, hiking, etc. Such a variation in atmospheric pressure is significant since IOP is typically in the range of about 15 mm Hg. Thus, for 24 hour monitoring of IOP, it is desirable to have pressure readings for the anterior chamber (as measured by P1) and atmospheric pressure in the vicinity of the eye (as measured by P3).

Therefore, in one embodiment of the present invention, pressure readings are taken by P1 and P3 simultaneously or nearly simultaneously over time so that the actual IOP can be calculated (as P1−P3 or P1−f(P3)). The pressure readings of P1 and P3 can be stored in memory 220 by processor 215. They can later be read from memory so that actual IOP over time can be interpreted by a physician.

Pressure sensors P1, P2, and P3 can be any type of pressure sensor suitable for implantation in the eye. They each may be the same type of pressure sensor, or they may be different types of pressure sensors. For example, pressure sensors P1 and P2 may be the same type of pressure sensor (implanted in the eye), and pressure sensor P3 may be a different type of pressure sensor (in the vicinity of the eye).

Figure 4:
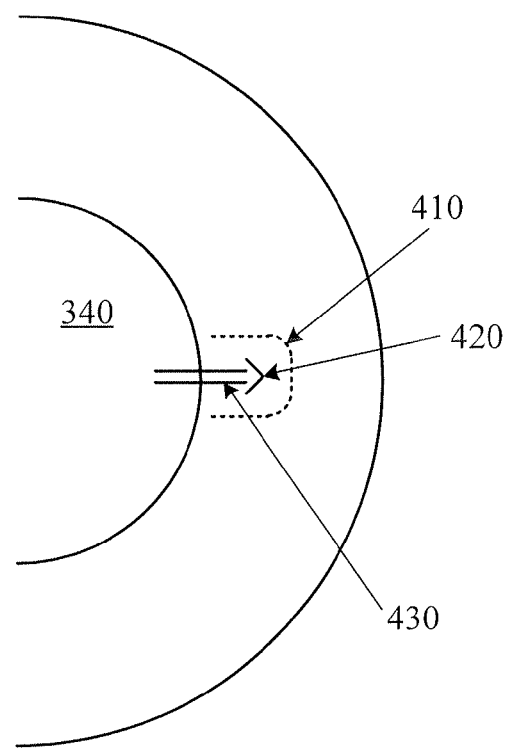
FIG. 4 is a diagram of one possible application of the IOP sensor of the present invention.

In another embodiment of the present invention, pressure readings taken by pressure sensors P1 and P2 can be used to control a device that drains aqueous from the anterior chamber 340. FIG. 4 is a diagram of one possible application of the IOP sensor of the present invention that utilizes the readings of pressures sensors P1 and P2. In FIG. 4, pressure sensor P1 measures the pressure in the anterior chamber 340 of the eye. Pressure sensor P2 measures the pressure at a drainage site 410.

Numerous devices have been developed to drain aqueous from the anterior chamber 340 to control glaucoma. Most of these devices are variations of a tube that shunts aqueous from the anterior chamber 340 to a drainage location 410. For example, tubes have been developed that shunt aqueous from the anterior chamber 340 to the subconjunctival space thus forming a bleb under the conjunctiva or to the subscleral space thus forming a bleb under the sclera. (Note that a bleb is a pocket of fluid that forms under the conjunctiva or sclera). Other tube designs shunt aqueous from the anterior chamber to the suprachoroidal space, the supraciliary space, the juxta-uveal space, or to the choroid. In other applications, tubes shunt aqueous from the anterior chamber to Schlemm's canal, a collector channel in Schlemm's canal, or any of a number of different blood vessels like an episcleral vein. Some tubes even shunt aqueous from the anterior chamber to outside the conjunctiva. Finally, in some applications, no tube is used at all. For example, in a trabeculectomy (or other type of filtering procedure), a small hole is made from the subconjunctival or subscleral space to the anterior chamber. In this manner, aqueous drains from the anterior chamber, through the hole, and to a bleb under the conjunctiva or sclera. Each of these different anatomical locations to which aqueous is shunted is an example of a drainage location 410.

In FIG. 4, a tube 430 with a valve 420 on one end is located with one end in the anterior chamber 340 and the other end in a drainage location 410. In this manner, the tube 430 drains aqueous from the anterior chamber 340 to the drainage location 410. Valve 420 controls the flow of aqueous from anterior chamber 340 to drainage location 410. Pressure sensor P1 is located in the anterior chamber or in fluid communication with the anterior chamber 340. As shown in the embodiment of FIG. 3, pressure sensor P1 is located upstream from valve 420. In this manner, pressure sensor P1 is located in the subconjunctival space but is in fluid communication with the anterior chamber 340.

Since pressure sensor P1 measures the pressure in the anterior chamber 340 and pressure sensor P2 measures pressure at the drainage location 410, the difference between the readings taken by these two pressure sensors (P1−P2) provides an indication of the pressure differential between the anterior chamber 340 and the drainage location 410. In one embodiment, this pressure differential dictates the rate of aqueous flow from the anterior chamber 340 to the drainage location 410.

One complication involved with filtering surgery that shunts the anterior chamber 340 to a drainage location 410 is hypotony—a dangerous drop in IOP that can result in severe consequences. It is desirable to control the rate of aqueous outflow from the anterior chamber 340 to the drainage location 410 so as to prevent hypotony. Readings from pressure sensor P1 and pressure sensor P2 can be used to control the flow rate through tube 430 by controlling valve 420. For example, valve 420 can be controlled based on the pressure readings from pressure sensor P1 and pressure sensor P2.

In another embodiment of the present invention, IOP (based on readings from pressure sensor P1 and pressure sensor P3) can be controlled by controlling valve 420. In this manner, IOP is the control parameter. Valve 420 can be adjusted to maintain a particular IOP (like an IOP of 15 mm Hg). Valve 420 may be opened more at night than during the day to maintain a particular IOP. In other embodiments, an IOP drop can be controlled. Immediately after filtering surgery, IOP can drop precipitously. Valve 420 can be adjusted to permit a gradual drop in IOP based on readings from pressure sensors P1 and P3.

In another embodiment of the present invention, readings from pressure sensor P2 (or from the difference between pressure sensor P2 and atmospheric pressure as measured by P3) can be used to control valve 420 so as to control the morphology of a bleb. One of the problems associated with filtering surgery is bleb failure. A bleb can fail due to poor formation or fibrosis. The pressure in the bleb is one factor that determines bleb morphology. Too much pressure can cause a bleb to migrate to an undesirable location or can lead to fibrosis. The pressure of the bleb can be controlled by using the reading from pressure sensor P2 (at drainage location 410—in this case, a bleb). In one embodiment of the present invention, the difference between the pressure in the bleb (as measured by P2) and atmospheric pressure (as measured by P3) can be used to control valve 420 to maintain a desired bleb pressure. In this manner, the IOP pressure sensor of the present invention can also be used to properly maintain a bleb.

Valve 420 can be controlled by microprocessor 215 or a suitable PID controller. A desired pressure differential (that corresponds to a desired flow rate) can be maintained by controlling the operation of valve 420. Likewise, a desired IOP, IOP change rate, or bleb pressure can be controlled by controlling the operation of valve 420.

While valve 420 is depicted as a valve, it can be any of a number of different flow control structures that meter, restrict, or permit the flow of aqueous from the anterior chamber 340 to the drainage location 410. In addition, valve 420 can be located anywhere in or along tube 430.

Finally, there are many other similar uses for the present IOP sensor. For example, various pressure readings can be used to determine if tube 420 is occluded or obstructed in some undesirable manner. As such, failure of a drainage device can be detected. In a self clearing lumen that shunts the anterior chamber 340 to a drainage location 410, an undesirable blockage can be cleared based on the pressure readings of P1, P2, and/or P3.

Figure 5:
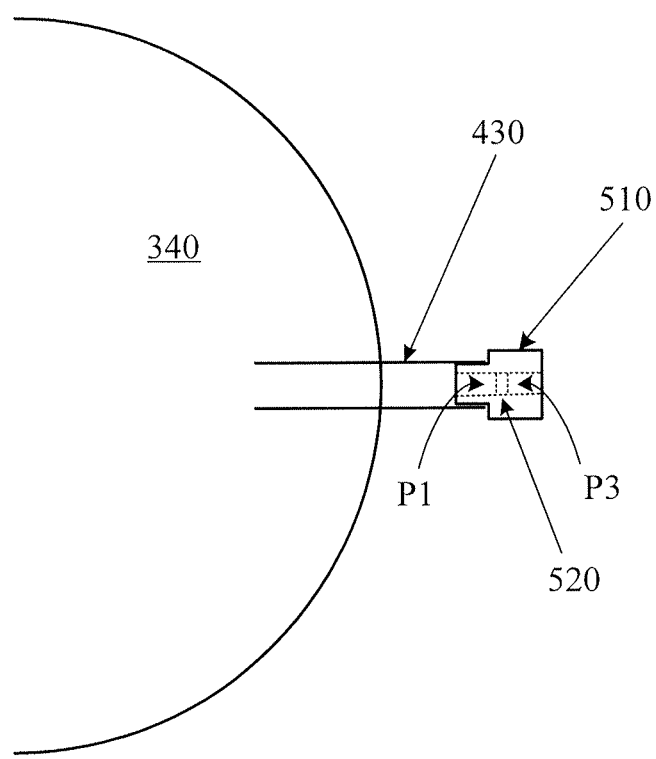
FIG. 5 is an end cap implementation of an IOP sensor consistent with the principles of the present invention.

FIG. 5 is an end cap implementation of an IOP sensor consistent with the principles of the present invention. In FIG. 5, pressure sensors P1 and P3 are integrated into an end cap 510. End cap 510 fits in tube 430 so as to form a fluid tight seal. One end of tube 430 resides in the anterior chamber 340, and the other end of tube 430 (where end cap 510 is located) is located outside of the anterior chamber 340. Typically, one end of tube 430 resides in the anterior chamber 340, and the other end resides in the subconjunctival space. In this manner, pressure sensor P1 is in fluid communication with the anterior chamber 340. Since there is almost no pressure difference between the anterior chamber 340 and the interior of tube 430 that is in fluid contact with the anterior chamber 340, pressure sensor P1 measures the pressure in the anterior chamber 340. Pressure sensor P3 is external to the anterior chamber 340 and either measures atmospheric pressure or can be correlated to atmospheric pressure.

Typically, tube 430 is placed in the eye to bridge the anterior chamber 340 to the subconjunctival space, as in glaucoma filtration surgery. In this case, P3 resides in the subconjunctival space. In this configuration, P3 measures a pressure that is either very close to atmospheric pressure or that can be correlated to atmospheric pressure through the use of a simple function. Since plug 510 provides a fluid tight seal for tube 430, pressure sensor P3 is isolated from pressure sensor P1. Therefore, an accurate IOP reading can be taken as the difference between the pressure readings of P1 and P3 (P1–P3). In one embodiment, a single, thin membrane 520 resides in the sensor package and is exposed to P1 on one side (tube side) and P3 on the other side (isolation side), and thus the net pressure on the membrane 520 is recorded by the sensor, providing a gauge reading corresponding IOP.

Figure 6A:
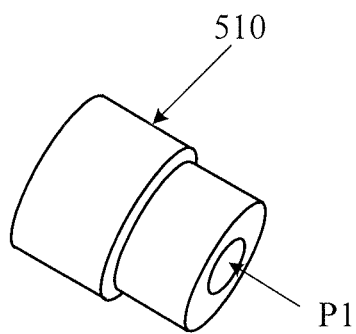
FIGS. 6A and 6B are perspective views of an end cap implementation of an IOP sensor consistent with the principles of the present invention.
Figure 6B:
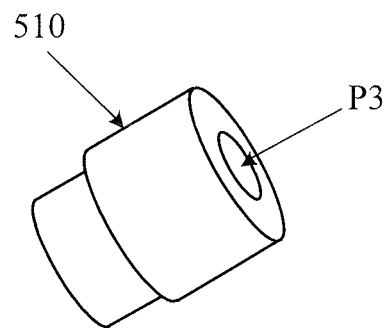

FIGS. 6A and 6B are perspective views of the end cap implementation of FIG. 5. In this embodiment, pressure sensor P1 is located on one end of end cap 510 so that it can be located inside tube 430. Pressure sensor P3 is located on the other end of end cap 510 so that it can be located outside of tube 430. A membrane (520) separates P1 from P3. In this manner, pressure sensor P1 is isolated from pressure sensor P3. While pressure sensors P1 and P3 are depicted as being located on opposite surfaces of a membrane 520 in the end cap 510, they can also be located integral with end cap 510 in any suitable position to facilitate the pressure measurements.

From the above, it may be appreciated that the present invention provides a system for measuring IOP. The present invention provides an IOP sensor with external pressure compensation. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A glaucoma treatment device comprising:
   an end cap with proximal and distal ends;
   an anterior chamber pressure sensor integrated with and located at the proximal end of the end cap and in fluid communication with an anterior chamber of an eye;
   a remote pressure sensor, the remote pressure sensor measures or approximates atmospheric pressure, the remote pressure sensor integrated with and located at the distal end of the end cap and under a conjunctiva of the eye; and
   a tube with proximal and distal ends, the tube fluidly coupling the anterior chamber to a location outside the anterior chamber wherein the end cap is located in and seals the distal end of the tube;
   wherein the end cap is configured to be located in the eye.

2. The glaucoma treatment device of claim 1 wherein the remote pressure sensor is located in a subconjunctival space of the eye.

3. The glaucoma treatment device of claim 1 further comprising:
   a membrane separating the anterior chamber pressure sensor from the remote pressure sensor.

4. The glaucoma treatment device of claim 1 wherein the remote pressure sensor approximates atmospheric pressure based on a correlation between a measured pressure and atmospheric pressure.

5. The glaucoma treatment device of claim 1 wherein the end cap is located in a subconjunctival space of the eye.

6. A glaucoma treatment device comprising:
   an end cap with proximal and distal ends, the end cap of a suitable size and shape to be located under a conjunctiva of an eye;
   an anterior chamber pressure sensor integrated with and located at the proximal end of the end cap and in fluid communication with an anterior chamber of an eye;
   a remote pressure sensor, the remote pressure sensor measures or approximates atmospheric pressure, the remote pressure sensor integrated with and located at the distal end of the end cap and under the conjunctiva of the eye; and
   a tube with proximal and distal ends, the tube of suitable size to be implanted in the eye, the tube fluidly coupling the anterior chamber to a location under the conjunctiva of the eye, wherein the end cap is located in and seals the distal end of the tube such that the proximal end of the end cap is located in the tube and the distal end of the end cap is located outside the tube.

7. The glaucoma treatment device of claim 6 further comprising:
   a membrane separating the anterior chamber pressure sensor and the remote pressure sensor.

8. The glaucoma treatment device of claim 6 wherein the remote pressure sensor approximates atmospheric pressure based on a correlation between a measured pressure and atmospheric pressure.

* * * * *